United States Patent [19]

Koya et al.

[11] 4,436,945

[45] Mar. 13, 1984

[54] METHOD OF HYDRO-DEALKYLATION

[75] Inventors: Masahiko Koya; Yohei Fukuoka, both of Kurashiki, Japan

[73] Assignee: Asahi Kasei Kogyo Kabushiki Kaisha, Osaka, Japan

[21] Appl. No.: 360,145

[22] Filed: Mar. 22, 1982

[30] Foreign Application Priority Data

Apr. 1, 1981 [JP] Japan .................................. 56-49193

[51] Int. Cl.$^3$ ............................................. C07C 4/12
[52] U.S. Cl. ..................................... 585/488; 585/486
[58] Field of Search ..................... 585/486, 488, 489

[56] References Cited

U.S. PATENT DOCUMENTS

| | | | |
|---|---|---|---|
| 3,236,761 | 2/1966 | Rabo et al. | |
| 3,240,697 | 3/1966 | Miele et al. | 585/486 |
| 3,716,596 | 2/1973 | Bowes | 585/486 |
| 3,926,782 | 12/1975 | Plank et al. | 585/486 |
| 4,218,573 | 8/1980 | Tabak et al. | 585/488 |

*Primary Examiner*—Curtis R. Davis
*Attorney, Agent, or Firm*—Spring, Horn, Kramer & Woods

[57] ABSTRACT

There is disclosed a method for producing benzene and other useful compounds in high yields and selectivity which comprises hydro-dealkylating alkyl aromatic hydrocarbons in the presence of hydrogen using a catalyst mainly composed of a zeolite 15 to 20 equivalent % of exchangeable cations of which are exchanged with hydrogen ions. The reaction temperature is preferably 500° to 650° C.

4 Claims, 2 Drawing Figures

METHOD OF HYDRO-DEALKYLATION

BACKGROUND OF THE INVENTION

This invention relates to an improved method for hydro-dealkylation of alkyl aromatic hydrocarbons and more particularly it relates to an improved method for producing useful compounds such as benzene and the like by catalytic hydro-dealkylation of alkyl aromatic hydrocarbons using a catalyst mainly composed of zeolite a part of exchangeable cations of which are exchanged with hydrogen ions.

Hitherto, for producing useful compounds such as benzene from alkyl aromatic hydrocarbons there has been widely used a method which comprises catalytically hydro-dealkylating the alkyl aromatic hydrocarbons using a catalyst, e.g., chromia or molbdena carried on alumina generally at a temperature of about 600° C.

However, this method has the difficulties that high temperatures are required for increasing productivity because said catalysts have no sufficient activity and use of high temperatures causes very serious deterioration of the catalysts. Furthermore, it has been generally known that various cation exchange zeolites possess catalytic activity for dealkylation reaction and disproportionation reaction of aromatic hydrocarbons. For example, there has been proposed a method for carrying out these reactions using, as catalysts, zeolites which are almost completely ion-exchanged with hydrogen ion which is a non-metallic cation. (See Japanese Patent Publication No. 25967/68). However, although zeolites which are cation exchanged with hydrogen ion by 50% or more have higher dealkylation activity as compared with conventional catalysts, they also have high disproportionation activity and so they are inferior in selectivity to provide undesired by-products and moreover they have high deterioration rate caused by deposition of coke.

As the result of the inventors' intensive researches to overcome these defects, it has been found that useful compounds such as benzene and the like can be obtained in high yield and selectivity by catalytic hydro-dealkylation of alkyl aromatic hydrocarbons using a zeolite having a specific hydrogen ion exchange ratio in the presence of hydrogen at a temperature of a specific range and that zeolites which contain a certain kind of metals as cations besides hydrogen ion are higher in stability and less in deterioration with time as hydro-dealkylation catalysts.

SUMMARY OF THE INVENTION

That is, this invention provides a method for hydro-dealkylation of alkyl aromatic hydrocarbons which comprises treating the alkyl aromatic hydrocarbons using a catalyst mainly composed of a zeolite 15 to 50 equivalent % of exchangeable cations of which are exchanged with hydrogen ions, at a temperature of 500° to 650° C.

DESCRIPTION OF PREFERRED EMBODIMENT

Figure 1:
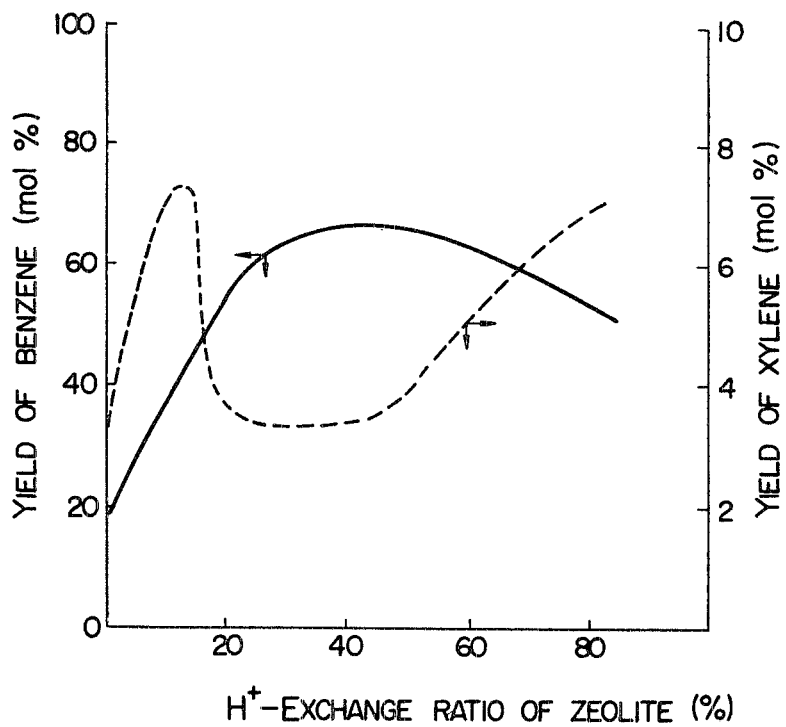
FIG. 1 is a graph which shows the relation between the hydrogen ion exchange ratio of catalyst and the yields of benzene and xylene in dealkylation reaction of toluene and FIG. 2 is a graph which shows the relation between elapsed time of dealkylation reaction of toluene and yield of benzene.

The zeolite used in this invention are preferably crystalline alumino silicate having a molar ratio of silica to alumina ($SiO_2/Al_2O_3$) of at least 2 and examples thereof are zeolites of type X, Y ZSM-5, etc. The ratio of exchange of alkali cations of these zeolites with hydrogen ions should be within the range of 15 to 50 equivalent % of exchangeable cations and preferably 20 to 40 equivalent %. When the hydrogen ion exchange ratio is less than 15 equivalent %, dealkylation activity is low and when it is more than 50 equivalent %, though the dealkylation activity is in high level, disproportionation reaction activity and high-boiling materials producing activity are also high and many undesired by-products are produced. Furthermore, deterioration of the zeolite catalyst becomes marked due to deposition of coke, etc.

Exchange of hydrogen ions for alkali cations of zeolites is usually effected by the method comprising dipping the zeolites in an aqueous ammonium salt solution to once exchange the alkali cations with ammonium ions and then calcining them at 300° to 500° C. to remove ammonia to make hydrogen ion type. However, for this invention it is suitable to dip zeolites in an aqueous acetic acid solution to directly exchange alkali cations with hydrogen ions.

The catalysts mainly composed of zeolite used in this invention preferably contain chromium metal or chromium metal and alkaline earth metals or rare earth metals as cation components besides hydrogen ions. For introducing these metals, for example, zeolites may be treated with an aqueous acetic acid solution containing chromium acetate or those which have been subjected to ion exchange with alkaline earth metals such as magnesium, calcium, etc. or rare earth metals may be treated with an aqueous acetic acid solution containing chromium acetate. Thus obtained catalysts are superior in stability and less in deterioration with time.

It is not clear why the catalyst compositions according to this invention are highly active as hydro-dealkylation catalyst, but the following can be guessed. That is, the catalysts obtained by the above treatments have less active points high in acid strength and have high distribution of active points of appropriate acid strength, because of which dealkylation activity increases and less by-products are produced. Furthermore, inclusion of chromium causes increase of hydrogen activation power, decrease of coke and decrease of deterioration with time, namely, increase the so-called stability.

As examples of alkyl aromatic hydrocarbons used in this invention, mention may be made of toluene, xylene, ethylbenzene and any alkyl aromatic hydrocarbons having at least 9 total carbon atoms, etc. These may be used alone or as a mixture. Furthermore, those which contain hydrocarbons such as paraffins, naphthenes, benzene etc. may also be used. Typical examples of such mixture raw materials are coke oven light oil, heart cut reformation, pyrolysis gasoline, etc.

Suitable conditions for hydro-dealkylation in this invention vary depending on compositions of raw materials, but it is desired that reaction temperature is 500° to 650° C., preferably 550° to 600° C., reaction pressure is 1 to 100 kg/cm$^2$, preferably 40 to 70 kg/cm$^2$, and raw material liquid feeding rate is 0.1 to 10, preferably 1 to 4 in liquid hourly space velocity (LHSV). Molar ratio of hydrogen to aromatic hydrocarbons is 1 to 10 mols, preferably 4 to 6 mols per 1 mol of the aromatic hydrocarbons.

When the reaction temperature is lower than 500° C., sufficient dealkylation rate cannot be obtained and when higher than 650° C., reduction of activity of the catalysts becomes marked.

Useful compounds such as benzene, etc. can be obtained in high yields and selectivities by catalytic hydrodealkylation of alkyl aromatic hydrocarbons according to the method of this invention. Furthermore, the catalyst compositions used in this invention are excellent in stability and less in deterioration with time.

The following non-limiting examples will illustrate this invention.

EXAMPLE 1

Commercially available zeolites Y (SK-40 manufactured by Union Carbide Co.) were dipped in aqueous acetic acid solutions of various concentrations which were heated to 70° to 80° C. to carry out $H^+$ exchange, and subjected to filtration, washing with water, drying (at 120° C. for 2 hours) and then heat-treatment in the air at 450° C. for 2 hours to obtain catalysts of various $H^+$ exchange ratios. These catalysts were packed in stainless steel reaction tubes of 10 mm $\phi \times 200$ mm and hydro-dealkylation reactions of toluene were effected (Experiment No. 1-1 to 1-4). Similarly, for comparison, dealkylation of toluene was effected using the commercially available dealkylation catalyst chromia alumina (Experiment No. 1-5). Experimental conditions and results are shown in Table 1. Relations between the $H^+$ exchange ratio of the zeolites and yield of benzene (indicated by solid line) and that of xylene (indicated by dashed line) are shown in FIG. 1.

It will be recognized from Table 1 and FIG. 1 that according to the method of this invention benzene can be obtained in a yield more than twice that compared with use of the chromia alumina which is a conventional dealkylation catalyst and that use of a $H^+$ exchange ratio of $H^+$ exchanged zeolite within the range of 20 to 45 equivalent % results in high benzene yield and less xylene yield which is a by-product produced by side-reaction. It will be also recognized that when the $H^{30}$ exchange ratio is 60%, the side-reaction gasification (hydrocracking of aromatic rings) is vigorous.

TABLE 1

| | Experiment No. | Kind of catalysts | Reaction conditions Temperature (°C.) | Pressure (kg/cm$^2$) | LHSV (Hr$^{-1}$) | H$_2$/Toluene (mol/mol) | Reaction liquid composition (mol %) Benzene | Toluene | Xylene | Rate of hydrocracking of aromatic rings |
|---|---|---|---|---|---|---|---|---|---|---|
| This invention | 1-1 | Zeolite Y H$^+$ exchange ratio 20% | 600 | 60 | 2.0 | 6.0 | 62 | 33 | 3.2 | 0.6 |
| This invention | 1-2 | H$^+$ exchange ratio 32% | 600 | 60 | 2.0 | 6.0 | 65 | 30 | 3.5 | 0.5 |
| Comparative | 1-3 | H$^+$ exchange ratio 13% | 600 | 60 | 2.0 | 6.0 | 37 | 53 | 7.4 | 0.4 |
| Comparative | 1-4 | H$^+$ exchange ratio 60% | 600 | 60 | 2.0 | 6.0 | 61 | 31 | 6.5 | 3.1 |
| Comparative | 1-5 | Cr$_2$O$_3$.Al$_2$O$_3$ | 600 | 60 | 2.0 | 6.0 | 28 | 71 | — | 0.4 |

Note 1:
Cation other than H$^+$ in the catalysts is Na$^+$.

Note 2:
Rate of hydrocracking of aromatic rings (Rate of gasification due to hydrocracking of aromatic rings in feed toluene) =
$$\frac{\text{Mol number of produced CH}_4 - (\text{mol number of produced benzene} - \text{mol number of produced xylene}) - \text{mol number of thiophene} \times 4}{\text{Mol number of charge toluene} \times 7} \times 100$$

EXAMPLE 2

A catalyst was prepared by dipping commercially available zeolite Y (SK-40 manufactured by Union Carbide Co.) in an aqueous acetic acid solution containing 10% chromium acetate, washing the zeolite with water, drying it and then heat-treating the zeolite dried with air at 450° C. for 2 hours.

A catalyst was prepared by dipping commercially available zeolite Y (SK-40 manufactured by Union Carbide Co.) repeatedly three times in a 42% aqueous calcium chloride solution at 70° to 80° C. for 30 minutes to perform sufficient calcium ion exchange, then washing it with water, drying it and then heat-treating it at 450° C. for 2 hours in the air. This catalyst had a Ca$^{2+}$ exchange ratio of 72 equivalent %. Another catalyst was prepared by further dipping this catalyst in an aqueous acetic acid solution containing 1% chromium acetate (pH 2.5) and then subjecting it to filtration, washing with water, drying and heat treatment at 450° C. for 2 hours in the air. Still another catalyst was prepared in the same manner as mentioned above except that Ce$^{2+}$ exchange was effected in place of Ca$^{2+}$ exchange and then the zeolite was subjected to the chromium acetate treatment. Dealkylation reaction of toluene was carried out using each of these catalysts. Experimental conditions and results are shown in Table 2.

TABLE 2

| | Experiment No. | Kind of catalysts | Reaction conditions Temperature (°C.) | Pressure (kg/cm$^2$) | LHSV (Hr$^{-1}$) | H$_2$/Toluene (mol/mol) | Reaction liquid composition (mol %) Benzene | Toluene | Xylene | Rate of hydrocracking of aromatic rings |
|---|---|---|---|---|---|---|---|---|---|---|
| This invention | 2-1 | H$^+$ exchange ratio 30% Cr$^+$ exchange ratio 10% | 600 | 60 | 2 | 6.0 | 62 | 32 | 4.6 | 0.3 |
| This invention | 2-2 | Ca$^{2+}$ exchange ratio 50% H$^+$ exchange ratio 35% Cr$^{3+}$ exchange ratio 5% | 600 | 60 | 2 | 6.0 | 67 | 28 | 3.0 | 0.4 |
| This invention | 2-3 | Ce$^+$ exchange ratio 40% H$^+$ exchange ratio 28% | 600 | 60 | 2 | 6.0 | 64 | 31 | 4.0 | 0.7 |

TABLE 2-continued

| Experiment No. | | Kind of catalysts | Reaction conditions | | | | Reaction liquid composition (mol %) | | | Rate of hydrocracking of aromatic rings |
|---|---|---|---|---|---|---|---|---|---|---|
| | | | Temperature (°C.) | Pressure (kg/cm²) | LHSV (Hr⁻¹) | H₂/Toluene (mol/mol) | Benzene | Toluene | Xylene | |
| Comparative | 2-4 | $Cr^{3+}$ exchange ratio 7% $Ca^{2+}$ exchange ratio 72% | 600 | 60 | 2 | 6.0 | 50 | 41 | 7.3 | 1.3 |

*Exchange ratios of Y zeolite base. The remainder is $Na^+$.
Feed liquid: toluene + 700 ppm thiophene

EXAMPLE 3

Using the catalyst obtained by treating a calcium ion exchanged zeolite Y with an aqueous acetic acid solution of chromium acetate in Example 2 (i.e., the catalyst of experiment No. 2-2), dealkylation of toluene was effected under the conditions of 610° C., 60 kg/cm², LHSV=1.5 hr⁻¹ and molar ratio hydrogen/toluene=6 and stability of the catalyst was examined. The results are shown in Table 3.

For comparison, similarly, stability was examined on the catalysts of experiments No. 1-2 and 1-4 of Example 1 ($H^+$ exchange ratio 32 equivalent % and 60 equivalent %, respectively). The results are shown in FIG. 2 together with those obtained hereinabove.

Figure 2:
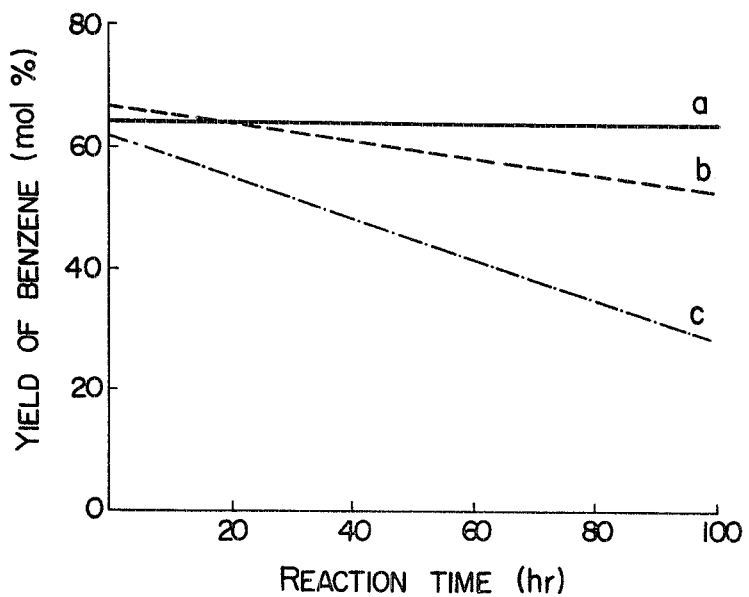

In FIG. 2, the result of this example is indicated by solid line (a), that of using the catalyst of experiment No. 1-2 is indicated by dashed line (b) and that of using the catalyst of experiment No. 1-4 is indicated by dash dotted line (c).

As is apparent from Table 2 of Example 2, Table 3 of Example 3 and FIG. 2 of Example 3, the zeolite catalysts obtained by exchange with calcium ions and subsequent treatment with chromium acetate are excellent catalysts which are higher in dealkylation activity and less in reduction activity with time and thus stable.

TABLE 3

| Lapsed reaction time (hr) | 5 | 10 | 25 | 50 |
|---|---|---|---|---|
| Yield of benzene (mol %) | 65 | 64 | 65 | 64 |
| Yield of heavy aromatics (mol %) | 1.5 | 1.5 | 1.5 | 1.5 |

Note 1 Feed liquid: toluene + 700 ppm thiophene
Note 2 Heavy aromatics: Condensates of aromatic rings, mainly, biphenyl

EXAMPLE 4

Effect of reaction temperature was examined on dealkylation reaction of toluene using the catalysts used in experiment No. 2-2 of Example 2. Conditions were 60 Kg/cm², LHSV=2 hr⁻¹, and molar ratio H₂/toluene=6. The results are shown in Table 4.

TABLE 4

| Reaction temperature | Reaction liquid composition (mol %) | | | |
|---|---|---|---|---|
| | Benzene | Toluene | Xylene | Heavy aromatics |
| 450° C. | 12 | 79 | 8 | 0.1 |
| 550° C. | 32 | 55 | 12 | 0.5 |
| 650° C. | 87 | 7 | 2 | 3.5 |

EXAMPLE 5

An aqueous solution of Q brand silicate (SiO₂ 28.9% by weight), an aqueous aluminum nitrate solution and an aqueous tripropylamine solution (10% by weight) in predetermined amounts were homogeneously mixed and the pH was adjusted to 10–10.5 with nitric acid. Thereafter, they were reacted under hydrothermal treatment conditions (180° C., 24 hr) and then calcined at 500° C. for 4 hours in the air to obtain ZSM-5 type zeolite (SiO₂/Al₂O₃=30), which was allowed to contact with a salt solution to obtain $Na^+$ exchanged Na type ZSM-5 zeolites.

In the same manner as in Examples 1 and 2, from these Na type ZSM-5 zeolites were produced $H^+$ exchanged ZSM-5 zeolites having $H^+$ exchange ratio of 40% and 70% and those having a $Ca^{2+}$ exchange ratio of 60% and these were treated with acetic acid or aqueous solution of chromium acetate. Dealkylation reactions of toluene were effected with the resultant catalysts.

Similarly, those which were ion-exchanged with rare earth metal $Ce^{2+}$ in place of $Ca^{2+}$ were prepared and used for the experiments.

Experimental conditions were 600° C., 60 Kg/cm², LHSV=2 hr⁻¹ and H₂/toluene molar ratio=6. The feed liquid was toluene+700 ppm thiophene. The results are shown in Table 5.

TABLE 5

| | Experiment No. | Catalysts (ZSM-5 Na type base) | Reaction liquid composition (mol %) | | |
|---|---|---|---|---|---|
| | | | Benzene | Toluene | Xylene |
| This invention | 5-1 | $H^+$ exchange ratio 40% | 47 | 37 | 14 |
| Comparative | 5-2 | $H^+$ exchange ratio 0% | 10 | 88 | 1 |
| Comparative | 5-3 | $H^+$ exchange ratio 70% | 37 | 35 | 25 |
| This invention | 5-4 | $Ca^{2+}$ exchange ratio 45% $H^+$ exchange ratio 32% | 51 | 36 | 12 |
| This invention | 5-5 | $Ca^{2+}$ exchange ratio 45% $H^+$ exchange ratio 33% $Cr^{3+}$ exchange ratio 5% | 52 | 36 | 10 |
| This invention | 5-6 | $Ce^{2+}$ exchange ratio 20% $H^+$ exchange ratio 33% $Cr^{3+}$ exchange ratio 10% | 48 | 37 | 13 |
| Comparative | 5-7 | $Ca^{2+}$ exchange ratio 60% | 35 | 43 | 20 |

The amount of coke on the catalyst of experiment No. 5-5 was further smaller than that on the catalyst of experiment No. 2-2 and was about 1/10 of the latter. Thus, the former catalyst was further superior in stability. (Comparison was made on the catalysts after the reaction for 10 hours.)

EXAMPLE 6

A Na type ZSM-5 zeolite produced in the same manner as in Example 5 was ion-exchanged with $Ca^{2+}$ and then treated with an aqueous acetic acid solution of chromium acetate in the same manner as in Example 2 to obtain a catalyst having a $Ca^{2+}$ exchange ratio of 40%, a $H^+$ exchange ratio of 30% and a $Cr^{3+}$ exchange ratio of 7%. Dealkylation reaction of pyrolysis gasoline was carried out using this catalyst. Reaction condition were 610° C., 60 Kg/cm², LHSV=2.0 hr$^{-1}$ and $H_2$/aromatics molar ratio=6. The results are shown in Table 6.

TABLE 6

| Experiment | | Reaction liquid composition (wt %) | | | | |
|---|---|---|---|---|---|---|
| | No. | Catalyst | Benzene | Toluene | Xylene | $C_9^+$ aromatics | |
| This invention | 6-1 | $H^+$, $Cr^{3+}$ and $Ca^{2+}$ exchanged ZSM-5 | 81 | 9 | 7 | 3 | 2% |

Composition of the pyrolysis gasoline ($C_5^-$ and $C_9^+$ were cut by distillation.)
$C_6$-$C_9$ paraffin, naphthene, (olefin)  24.9 wt %

| | |
|---|---|
| Benzene | 38.1 wt % |
| Toluene | 24.6 wt % |
| $C_8$ aromatics | 12.4 wt % |

What is claimed is:

1. A method for hydro-dealkylation of an alkyl aromatic hydrocarbon which comprises treating the alkyl aromatic hydrocarbon in the presence of hydrogen using a catalyst mainly composed of a zeolite 15 to 50 equivalent % of exchangeable cations of which are exchanged with hydrogen ions.

2. A method according to claim 1 wherein the catalyst is mainly composed of zeolite which is hydrogen ion exchanged by treatment with acetic acid.

3. A method according to claim 1 or 2 wherein the catalyst mainly composed of zeolite contains chromium metal or chromium metal with the alkaline earth metal or a rare earth metal as cation component besides hydrogen ion.

4. A method according to claim 1 wherein the hydrodealkylation is carried out at a temperature of 500° to 650° C.

* * * * *